United States Patent [19]

Griffin

[11] 4,335,730
[45] Jun. 22, 1982

[54] COLLECTOR ASSEMBLY AND SPECIMEN TUBE THEREFOR

[76] Inventor: Gladys B. Griffin, 848 S. Johnson Ct., Lakewood, Colo. 80226

[21] Appl. No.: 71,235

[22] Filed: Aug. 30, 1979

[51] Int. Cl.³ .......................................... A61B 10/00
[52] U.S. Cl. .................................. 128/760; 128/295; 141/331; 422/102
[58] Field of Search ........................ 128/760–766, 128/295, 771; 4/454, 462, 463, 479; 73/421 R; 210/DIG. 23, DIG. 24, 516; 141/331, 344, 339, 337; 422/72, 102; 233/26; D24/22

[56] References Cited

U.S. PATENT DOCUMENTS

| | | | |
|---|---|---|---|
| 1,733,261 | 10/1929 | Higby et al. | 141/337 |
| 2,700,973 | 2/1955 | Ju | 128/771 |
| 3,481,712 | 12/1969 | Bernstein | 422/102 |
| 3,518,164 | 6/1970 | Andelin et al. | 128/760 X |
| 3,615,222 | 10/1971 | Mead | 422/72 X |
| 3,711,871 | 1/1973 | Sherin | 128/760 X |
| 3,832,738 | 9/1974 | Kliemann | 128/761 X |
| 3,871,231 | 3/1975 | Ciarico | 128/295 X |
| 3,923,040 | 12/1975 | Beach | 128/760 X |
| 4,026,433 | 5/1977 | Crippa | 128/761 X |
| 4,106,490 | 8/1978 | Spilman et al. | 128/771 X |
| 4,106,907 | 8/1978 | Charlton et al. | 422/72 X |
| 4,116,066 | 9/1978 | Mehl et al. | 128/760 X |
| 4,187,861 | 2/1980 | Heffernan | 128/764 |

FOREIGN PATENT DOCUMENTS

| | | | |
|---|---|---|---|
| 2144176 | 3/1973 | Fed. Rep. of Germany | 128/295 |
| 1195492 | 6/1970 | United Kingdom | 422/102 |

*Primary Examiner*—Lee S. Cohen

[57] ABSTRACT

A urine specimen collector assembly includes a specimen tube and funnel-shaped member wherein the specimen tube is characterized by having a lower reinforced reservoir tip of reduced diameter so that the tube is adapted for use with centrifuge machines for the precipitation of a measured quantity of solid materials in the tip from the specimen placed in the tube. The mouth of the tube is outwardly flared to conform to the shape of the outlet end of the funnel, and the funnel has a ribbed internal surface to direct the flow of liquid through an elongated outlet tip for insertion into the specimen tube so that the tube and funnel may be filled with fluid. Upon inversion, a user may empty all but a measured quantity of fluid from the tube.

16 Claims, 10 Drawing Figures

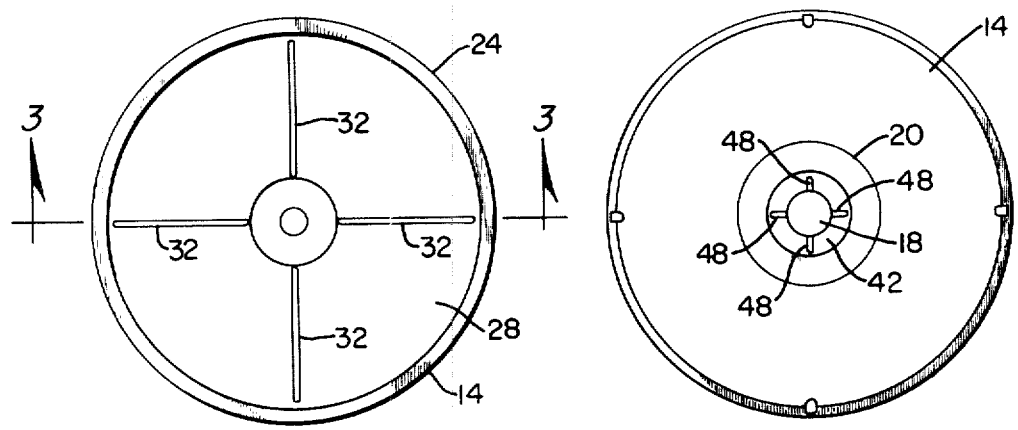
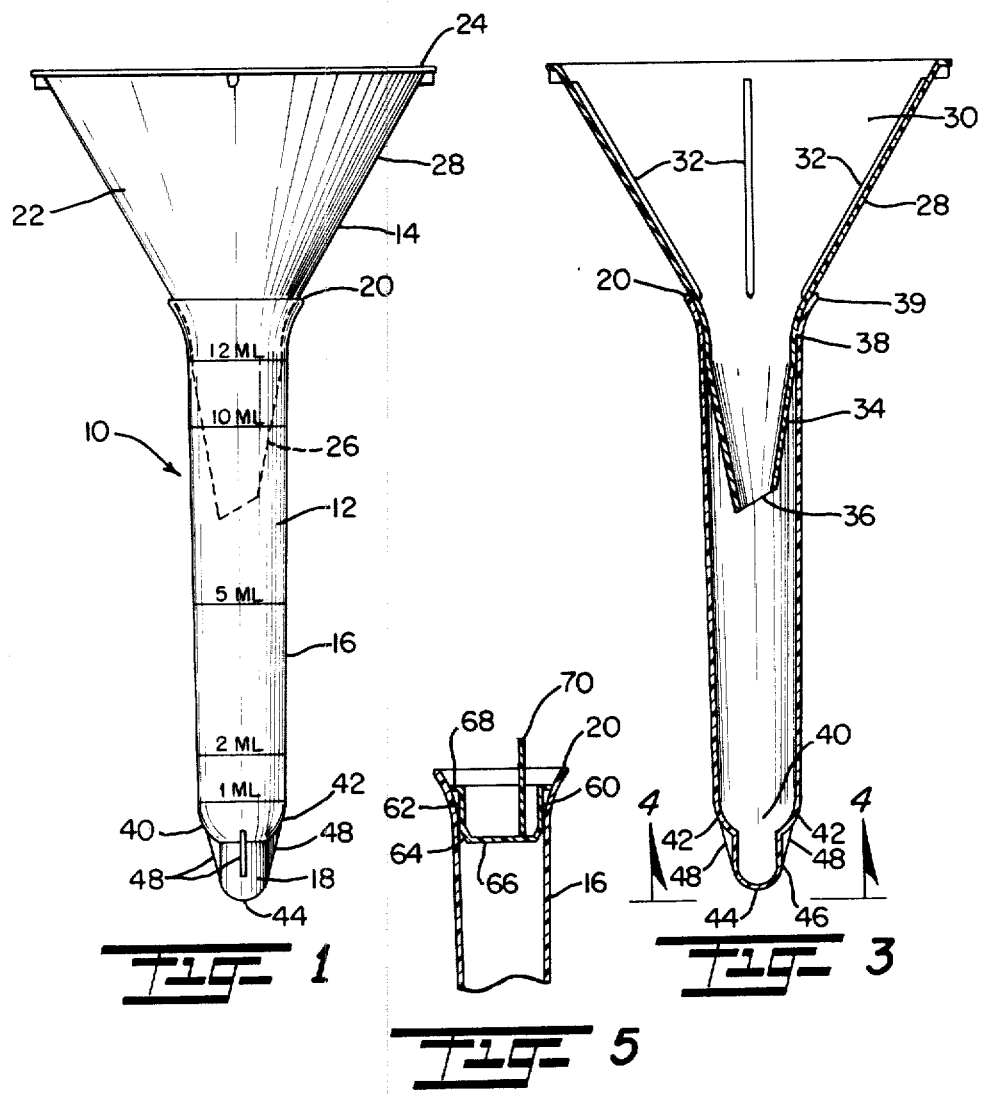

COLLECTOR ASSEMBLY AND SPECIMEN TUBE THEREFOR

The present invention relates to liquid specimen collector and testing devices specifically of the type adapted for the sanitary sampling of human urine as an indicator of various pathological conditions. As is often the case, it is desirable to obtain such a sample free from bacteria present in the body or in the urethra. Such a specimen is taken during the middle of the period of urination so that it is taken "in midstream" utilizing the inherent property of the urine to wash away extraneous bacteria to provide a relatively uncontaminated sample of urine.

BACKGROUND OF THE INVENTION

Heretofore, it has been well known to utilize a cup or jar or similar container to collect the urine specimen from the patient by having the patient urinate directly into the container. In practice, however, the container of urine may often be exposed unduly to airborne bacteria and contamination and may be contaminated from other sources as well. For example, it is often necessary that the specimen be transferred to various testing containers, such as, centrifuge tubes and the like, and additional contamination may thereby result. Further contamination may occur when the analyzing technician requires a measured quantity of a specimen so that it is necessary to utilize several receptacles for purposes of the measurement and storage of the selected quantity. Contamination can also occur due to bacteria on the surface of the opening of the specimen collector container or through overflow or imprecise filling of the container.

Midstream collectors have been developed in the past which have recognized the problems of contamination of the specimen. For example, U.S. Pat. No. 3,832,738 to Kliemann issued Sept. 3, 1974 and U.S. Pat. No. 3,711,871 to Sherin issued Jan. 23, 1973 disclose sanitary liquid specimen collectors having enlarged mouths and tops to seal these mouths after the specimen has been collected. U.S. Pat. No. 3,923,040 to Beach issued Dec. 2, 1975 discloses the use of a graduated tube having a funnel with a flexible spout wherein the entire assembly is sealed by a cap fitting around the specimen tube and spout. In this apparatus, the collector tube is in the form of a common centrifuge tube so that it may be utilized for analysis purposes as well. Similarly, U.S. Pat. No. 3,518,164 issued June 30, 1970 to Andelin et al, U.S. Pat. No. 4,026,433 issued May 31, 1977 to Crippa and U.S. Pat. No. 4,106,490 issued Aug. 15, 1978 to Spilman et al all disclose sanitary urine collection apparatus including a graduated tube which may be utilized for analysis purposes, especially with a centrifuge apparatus. A problem in the prior art, though, has been the danger of breakage of the specimen tube when centrifuged, especially where the collector tube is formed with a sediment trap at its lower end. Indeed, no prior art known to the applicant has successfully incorporated a collector tube with a small sediment trap at its closed end which sediment trap is constructed to withstand the forces of centrifuging.

The present invention, however, provides a novel specimen collector which allows the sampling of a midstream portion of fluid in such manner as to allow the disposal of the excess fluid while providing a measured amount thereof. Further, the present device has a reinforced sediment trap and is adaptable for use with standard centrifuge machines without requiring transfer of the fluid to a special centrifuge tube.

SUMMARY OF THE INVENTION

It is therefore an object of the present invention to provide a novel and improved urine specimen collector device as a sanitary and effective means for collecting and analyzing samples of human urine.

Another object of the present invention is to provide a convenient means for collecting urine specimens occurring "midstream" directly into a specimen tube.

Another object of the present invention is to provide a urine specimen collector which allows collection of a urine sample in a minimum number of steps while minimizing the risk of contamination.

Still another object of the present invention is to provide a two-piece urine collector which allows the user to discard excess of the sample while automatically providing a measured quantity for analysis all under sanitized conditions.

Still a further object of the present invention is to provide a urine collector assembly wherein the sample is conducted directly into an analysis tube having a reduced portion of measured volume to retain a measured amount of fluid upon inversion of the analysis tube and to receive solid precipitate from that sample during centrifuge analysis.

Yet another object of the present invention is to provide a urine collector assembly including a funnel and centrifuge tube which are configured for collecting a controlled volume sample of the "midstream" portion of urine in which a vapor lock is established between the funnel and tube; and wherein the surface tension of the fluid in a reduced portion of the tube is such that a simple yet accurately measured volume of liquid sample or solid precipitate can be collected while avoiding undue contamination of the sample by the user.

In accomplishing these objects, the novel and improved urine collector assembly according to the preferred embodiment of the present invention comprises an improved funnel and centrifuge tube each specially constructed as herein described. Specifically, the present invention is adapted to be used to collect a midstream portion of a urine specimen and includes an elongated collector tube adapted to be employed with centrifuge machines and which tube has a lower reinforced reservoir tip at one closed end and an outwardly flared mouth at an open end opposite the reservoir tip. The reservoir tip is of a selected volume and is generally cylindrical having a mouth of reduced diameter with respect to the main body of the tube. Upon inversion of the tube, the surface tension of the specimen fluid in the tip causes the tip to retain a measured amount of fluid. The reservoir tip also receives solid precipitate during the centrifuging operation. In order to permit use of the collector tube during the centrifuging operation, the reservoir tip has thickened sidewall portions preferably in the form of a plurality of circumferentially spaced external reinforcement ribs extending in a longitudinal direction from the sidewall of the reservoir tip of the centrifuge collector tube whereby to support the reservoir tip and reinforce it in circumferential and longitudinal directions.

In order to facilitate collection and to enhance sanitary collection of the specimen, the collector assembly includes a funnel-shaped member having a conical sidewall and an elongated spout provided with an angled tip or discharge end which is adapted to be inserted into the main body portion of the collector tube. The collector tube has an outwardly flared mouth opposite the reservoir tip which is shaped to conform to the external surface of the funnel so that the funnel may firmly seat and be sealed in the mouth of the collector tube, and the mouth provides a lip constructed to snap-fit with a sealing lid. Further, the funnel has a plurality of ribs on its internal surface to direct the flow of fluid toward the elongated spout for conducting the fluid into the collector tube.

The collector tube is graduated so that the volume of liquid contained therein may be readily observed. A feature of the present invention resides in the selection of length and size of the elongated spout of the funnel and the seating of the funnel surface against the flared mouth of the collector tube. Particularly, the seating of the funnel and mouth of the collector tube establish a vacuum or vapor lock when fluid is introduced into the collector tube through the funnel to prevent overflow; and, upon inversion of the apparatus, any portion of the sample in the funnel may be exhausted. Therefore, the positioning of the mouth of the elongated tip defines the amount of fluid which will remain in the collector tube so that a standard measurement quantity may automatically be retained.

By constructing the funnel and tube out of a plastic or plastic-like material, an inexpensive apparatus may be provided and, if desired, this apparatus may be disposable. Further, by constructing the apparatus out of inexpensive materials, contamination can be reduced by avoiding the need for reuse of the collector apparatus. Contamination is also minimized in operation when a sample is placed in the collector tube and automatically measured by inverting the apparatus with the collector tube subsequently being usable in a centrifuge so that there is no need to contaminate the sample by transferring it to a special receptacle.

These and other objects, advantages and features will become more readily appreciated and understood when taken together with the following detailed description in conjunction with the accompanying drawings, in which:

BRIEF DESCRIPTION OF THE DRAWINGS

FIG. 1 is a front elevational view of the midstream collector assembly according to the preferred embodiment of the present invention;

FIG. 2 is a top plan view of the collector assembly according to the preferred embodiment of the present invention;

FIG. 3 is a cross-sectional view of the preferred embodiment of the present invention taken about lines 3—3 of FIG. 2;

FIG. 4 is a bottom plan view of the preferred embodiment of the present invention taken about lines 4—4 of FIG. 3;

FIG. 5 is a cross-sectional view of the upper portion of the preferred collector tube including a sealing plug therefor;

DETAILED DESCRIPTION OF THE PREFERRED EMBODIMENT

Figure 6:
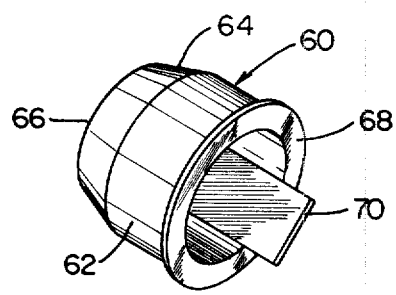
FIG. 6 is a perspective view of the sealing plug shown in FIG. 5.

The preferred embodiment of the present invention is a novel urine specimen collector apparatus especially adapted to sample human urine "midstream". Its construction allows for ease of operation while avoiding the tendency for contamination by being fabricated out of inexpensive, discardable materials; and further is so constructed as to be directly employable with a standard centrifuge apparatus for analyzing the contents of the specimen collected by the assembly. The assembly further is constructed to automatically measure a desired quantity of specimen while obviating the transfer of fluid contained therein.

As is shown in FIG. 1, collector assembly 10 includes a graduated collector tube 12 and a funnel 14. Tube 12 has an elongated cylindrical main body 16 which is closed at one end by a sediment trap in the form of a reservoir tip 18 and which has an outwardly flared mouth 20 with an exposed edge 39 at an end opposite reservoir tip 18. Funnel 14 is adapted to be inserted into collector tube 12 and includes a conical body portion 22 which has an upper circular rim 24 and an elongated spout 26 opposite circular rim 24 at the vortex of conical body portion 22. As is shown in FIGS. 2 and 3, funnel 14 has a smooth uninterrupted outer surface 28 and is provided on its interior surface 30 with a plurality of circumferential spaced, axially extending ribs 32. Ribs 32 function to direct or guide a fluid sample entering funnel 14 towards spout 26 for discharge into collector tube 12.

Elongated spout 26 is tapered so that its sidewall 34 converges from a generally cylindrical portion 38 into an angled tip at its lower open end 36. Open end 36 is preferably formed in a plane that is oblique to the longitudinal axis of funnel 14 and functions as is hereinafter described. As may be noted in FIG. 3, cylindrical midportion 38 of funnel 14 is configured in a shape which conforms to that of flared mouth 20 of collector tube 12 so that an annular portion of funnel 14 abuts the upper frustoconical portion 39 of flared mouth 20 of collector tube 12.

An important feature of the present invention is found in the construction of the closed end 40 of collector tube 12. Closed end 40 is formed by a rounded, downwardly convergent end wall 42 of main body 16 to which is attached a closed cylindrical reservoir tip 18 which is coaxial with main body 16 to define a sediment trap in the form of a cylindrical nose portion of tube 12. As noted, reservoir tip 18 has a closed rounded tip 44 and a cylindrical sidewall 46 with cylindrical sidewall 46 having a smaller diameter than main body 16. A particular problem among the prior art in forming a reservoir tip such as tip 18 has been the fragile nature of this construction so that the tube is not readily adaptable to analytical measurement machines for fear of breakage. The present invention, however, removes this disadvantage by having a plurality of support ribs 48 at equally spaced intervals around the reservoir tip 18 defining thickened sidewall portions therefor, with these thickened sidewall portions being somewhat thicker than main body 16. Specifically, ribs 48 extend lengthwise and are tapered downwardly from rounded end wall 42, along cylindrical sidewall 46 to points adjacent tip 44 of reservoir tip 18. In this manner, the entire length of reservoir tip 18 is reinforced by ribs 48 along spaced intervals about its sidewall 46. While in the preferred embodiment four such ribs 48 are provided, any number may be employed so long as suitable reinforcement is present for tip 18. Ribs 48 are generally triangular and somewhat fin-shaped and may be of the same thickness as the sidewall of collector tube 12, but may also be fabricated with a reduced thickness on the order of one-half that of the sidewall of tube 12. It is important, however, to increase substantially the effective thickness and strength of the sidewall of tip 18 so as not to be subject to breakage during a centrifuging procedure. As shown in FIGS. 1 and 3, ribs 48 are triangularly shaped so as to join end wall 42 and tip 44 while having a sufficient width so that the unconnected inclined edge of the triangle tapers or converges downwardly a line between the sidewall of collector tube 12 and the end of reservoir tip 44.

Figure 7:
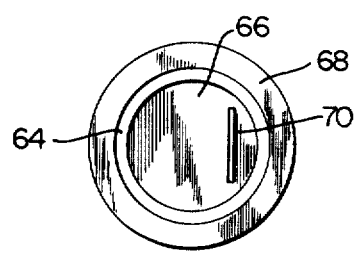
FIG. 7 is a top plan view of the sealing plug shown in FIGS. 5 and 6.

To seal collector tube 12 once a sample has been placed therein, two different types of sealing caps are provided in the present invention as is shown in FIGS. 5 through 9. The first form of sealing cap is shown in FIGS. 5-7 and comprises a plug 60 adapted to be inserted into flared mouth 20 and into a portion of main body 16 so that it is frictionally retained therein. Plug 60 has a cylindrical sidewall 62 which has a tapered nose 64 terminating in a flat end wall 66. Sidewall 62 has an upper surrounding shoulder 68 opposite end wall 66 which is configured to abut flared mouth 20 when inserted in collector tube 12 as shown in FIG. 5. Tab 70 is attached to end wall 66 internally of sidewall 62 and extends outwardly of plug 60 so that it may be easily gripped by the user to withdraw plug 60 from collector tube 12.

Figure 8:
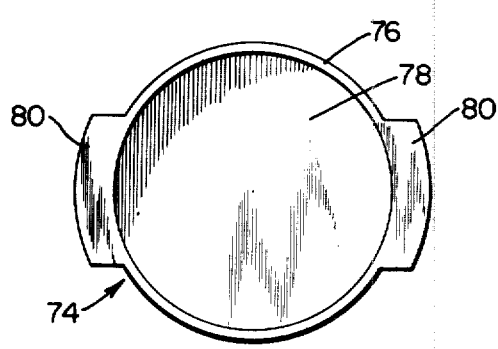
FIG. 8 is a bottom plan view of an alternate sealing cap for the collector tube according to the present invention.
Figure 9:
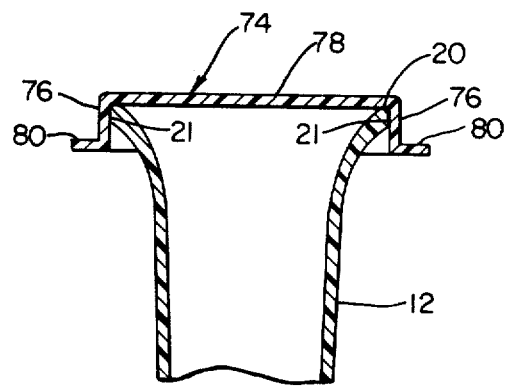
FIG. 9 is a cross-sectional view of the upper portion of the collector tube with the sealing cap shown in FIG. 8 attached thereto.

The second type of sealing cap, shown in FIGS. 8 and 9, is adapted to snap fit over the flared mouth 20 of collector tube 12 as shown in FIG. 9. Cap 74 has a cylindrical sidewall 76 and a flat end wall 78 and a pair of diametrically opposed shoulders 80 to facilitate attachment and removal of cap 74 from collector tube 12. Sidewall 76 and end wall 78 therefore form a cylindrical cavity into which flared mouth 20 may be inserted with the opening of this cavity configured to be resiliently biased so that it is frictionally retained on flared mouth 20 as shown in FIG. 9. Collector tube 12, as shown in FIG. 9, preferably has a surrounding flat rim portion 21 which provides an annular abutting surface for contacting the interior surface of sidewall 76. Shoulders 80 form flat, lateral projections from sidewall 76 whereby leverage may be exerted to pry cap 74 from collector tube 12.

Figure 10:
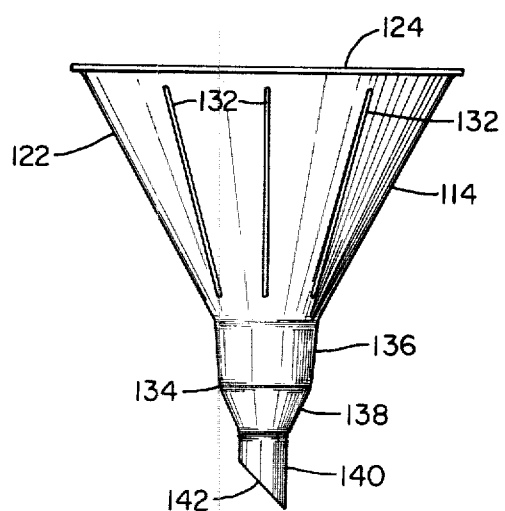
FIG. 10 is a modified funnel member adaptable to the collector tube of the present invention.

FIG. 10 shows an alternate embodiment of a funnel member 114 which is compatible with collector tube 12. Funnel 114 has an upper portion similar to funnel 14 with funnel 114 including a conical body portion 122 having a circular rim 124 with a plurality of ribs 132 formed on the interior surface of body portion 122. A somewhat different spout is constructed opposite rim 124, with a spout assembly 134 being formed in open communication with the interior of body portion 122. Specifically, spout assembly 134 has a slightly tapered, but generally cylindrical section 136, a frustrum 138 and a cylindrical tip 140 having an angled or oblique opening 142. Tip 140 generally has the same diameter of spout 34 at its open end 36. In use, spout assembly 134 is inserted into flared mouth 20 of collector tube 12. Cylindrical section 136 is sized for close fitting engagement with the interior of flared mouth 20 so as to allow edge 39 to abut the exterior of body portion 122, similar to the manner as shown in FIG. 3. However, by slightly tapering section 135, a frictional seal is achieved between the exterior sidewall of section 136 and the interior sidewall of flared mouth 20.

Utilization of the collector tube and funnel according to the present invention may now be appreciated with respect to the particular configuration of funnel 14 and flared mouth 20 as well as reservoir tip 18. In use, funnel 14 is placed in collector tube 12 so that midportion 38 abuts flared mouth 20 around an annular portion of collector tube 12. The patient then fills collector tube 12 with a biological specimen by means of funnel 14 so that the biological specimen fills collector tube 12 and covers open end 36 of elongated spout 26. This creates a vapor lock at a fluid level defined by the position of open end 36 so that excess fluid does not enter tube 12. If an excess of the specimen is taken so that the fluid level extends into funnel 14, the patient may drain the excess fluid. An automatically measured amount of fluid is therefore obtained by the vacuum seal. After the measured amount of fluid is provided in collector tube 12, the sample may be sealed either with plug 60 or cap 74. At this point, the sample is ready for analysis.

Preferably the spout has an internal diameter of approximately 0.65 cm or 0.25 inch where a urine specimen is to be collected. It is important, for a selected fluid, that the diameter of the spout be sufficiently large to allow venting of the air in the collector tube. If the diameter is too small, the surface tension of a viscous fluid will cause the stream of fluid entering the funnel member to seal the spout thereby preventing the escape of air from the collector and consequently preventing entry of fluid into the collector tube.

An advantage gained by cutting the spout opening at an oblique angle is realized when the user pours excess fluid out of the funnel. Particularly, if the tube and funnel assembly is tilted so that the fluid level in the collector tube (defined by the vacuum seal at the spout opening) approaches a somewhat parallel position relative to the oblique plane of the opening, the vacuum seal will not be broken. This latter, undesired event may occur where a perpendicular spout opening is employed since, when the assembly is tilted, approximately one-half of the opening is exposed and the vacuum seal is only then maintained by the surface tension of the fluid at the opening. This type of seal is, of course, very unstable for this system.

Further preparation for analysis of the sample may be undertaken directly in collector tube 12 since, by having reinforced reservoir tip 18, the sample may be directly centrifuged without the need for transferring containers. Reservoir tip is sized to have a volume of 0.25 milliliters in the preferred embodiment but may be sized for other volumes such as 0.5 milliliters, 1.0 milliliters or in another desired volume. When a urine specimen is centrifuged, then, in collector tube 12, then, suspended solids are then collected and concentrated in reservoir tip 18 to form a sediment or semi-solid material having the volume of reservoir tip 18. The fluid portion of the sample may then be transferred to another container or disposed of with the solid plug of material being ready for further analysis as a premeasured volume. Reservoir tip 18 also permits the automatic measuring of an amount of fluid corresponding to its volume upon inversion of tube 12 since the diameter of its mouth is relatively small so that the surface tension of the fluid holds the fluid in the reservoir tip. Analysis of the fluid may then be conducted.

It will be evident that while the preferred form of this invention has been described specifically in conjunction with its use for urine specimen analysis, it is conformable for use in other applications, such as for instance, radioimmunoassay determinations. Generally, therefore, it has application to any determination in which a limited but measured volume of material is to be collected and analyzed. Accordingly, although the present invention has been described with particularity relative to the foregoing detailed description of the preferred embodiment, various modifications, changes, additions and applications other than those specifically mentioned herein will be readily apparent to those having normal skill in the art without departing from the spirit and scope of this invention.

I claim:

1. A specimen collector tube unit adaptable for collecting urine specimens therein comprising:
    an elongated tubular member having an open end, a closed end opposite said open end, a surrounding sidewall portion between said open end and said closed end terminating in a rounded convergent end wall adjacent to said closed end, and a reservoir tip at said closed end defining an axial extension of said end wall and being of substantially the same wall thickness as said surrounding sidewall portion, the degree of convergency of said rounded convergent end wall into said reservoir tip being sufficient to prevent the release of that portion of a urine specimen contained in said reservoir tip when said elongated tubular member is inverted to pour out the urine specimen from said elongated tubular member and external reinforcing means extending between and united with said reservoir tip and said rounded convergent wall.

2. A specimen collector unit according to claim 1, wherein said reinforcing means are defined by a plurality of longitudinally extending, circumferentially spaced reinforcement ribs between the external surface of said end wall and said reservoir tip.

3. A specimen collector unit according to claim 1 wherein said reservoir tip has an axial length and a diameter sufficient to retain a fluid specimen having a volume of between 0.25 and 1.0 milliliter, inclusively.

4. A specimen collector unit according to claim 1 wherein said open end is defined by an outwardly flared mouth having a frusto-conical sidewall portion.

5. A specimen collector unit comprising:
    an elongated tubular member having a cylindrical sidewall portion, an outwardly flared mouth portion at one end, said cylindrical sidewall portion terminating at the other end of said tubular member in a rounded convergent end wall, and a reservoir tip attached to said end wall in open communication with the interior of said tubular member, with said end wall converging sharply into said reservoir tip to form an edge at their juncture, said reservoir tip enclosed on one end and coaxially aligned with said cylindrical sidewall portion; and
    longitudinally extending external reinforcement means extending between said end wall and said reservoir tip for reinforcing the juncture between said end wall and said reservoir tip.

6. A specimen collector unit according to claim 5 wherein said reinforcement means includes at least one external rib extending axially of said reservoir tip.

7. A specimen collector unit according to claim 5 wherein said reinforcement means includes a plurality of downwardly tapered ribs equally spaced around the perimeter of said reservoir tip and each said rib having an exposed edge forming a tapered extension between said end wall and said reservoir tip and having a thickness approximately one half the thickness of said cylindrical sidewall portion.

8. A specimen collector unit according to claim 5, further including sealing means for sealing said flared mouth portion, said sealing means frictionally engageable with said flared mouth portion.

9. A specimen collector unit according to claim 8 wherein said sealing means is a plug member frictionally secured internally of said flared mouth portion.

10. A specimen collector unit according to claim 8 wherein said sealing means is a cap member having a flat sealing surface and a projecting surrounding rim frictionally receiving the edge of said flared mouth portion for resiliently retaining said cap member thereon.

11. A urine specimen collector assembly comprising:
    a funnel-shaped member having a generally conical sidewall and an elongated spout attached at the vertex thereof in fluid communication with the interior of said funnel-shaped member, the exterior of said conical sidewall being substantially smooth and uninterrupted, said spout having an opening at an end opposite said vertex;
    an elongated tube releasably connected to said funnel-shaped member having a first end defined by an outwardly opening mouth including an interior surface dimensioned for and in close-fitting, mating abutment with the exterior surface of said funnel-shaped member with said spout extending into said tube, a cylindrical midportion, and a second end opposite said first end having a reservoir tip in the form of a cylindrical nose and an end wall converging sharply into said reservoir tip from said cylindrical midportion, said reservoir tip having an internal diameter less than the internal diameter of said cylindrical midportion, the degree of convergency of said end wall into said reservoir tip being sufficient to prevent the release of that portion of a urine specimen collected in said reservoir tip when said elongated tube is inverted to pour out the balance of the urine specimen from said elongated tube; and
    longitudinal reinforcement ribs extending between said end wall and said reservoir tip.

12. A urine specimen collector assembly according to claim 11, wherein said funnel-shaped member includes a fluid guide rib on its interior surface.

13. A urine specimen collector assembly according to claim 11 wherein said spout opening is formed in a plane oblique to the longitudinal axis of said spout.

14. A urine specimen collector assembly for the measured collection of a fluid specimen comprising:
    an elongated collector tube having an open end and a closed end, a surrounding sidewall portion between said open end and said closed end terminating in a rounded convergent end wall adjacent to said closed end, and a reservoir tip at said closed end defining an axial extension of said end wall and being of substantially the same wall thickness as said surrounding sidewall portion, the degree of convergency of said rounded convergent end wall into said reservoir tip being sufficient to prevent the release of that portion of a urine specimen contained in said reservoir tip when said elongated tube is inverted to pour out the urine specimen from said elongated tube and external reinforcing means extending between and united with said reservoir tip and said end wall;

a funnel-shaped member having a generally conical sidewall and an elongated spout attached thereto in fluid communication with the interior of said funnel-shaped member, said spout having a generally cylindrical portion adjacent said conical sidewall configured for and in close-fitting engagement with the interior of said collector tube adjacent said open end whereby said funnel-shaped member is frictionally retained in said collector tube; and said spout terminating in a downwardly tapered open end having a diameter of approximately one-half the diameter of said collector tube, said cylindrical portion extending into the interior of said collector tube and said tapered open end projecting into said collector tube being of a limited size to define a vapor seal for said fluid between said tapered open end and said collector tube.

15. A urine specimen collector assembly according to claim 14 wherein said tapered open end is formed obliquely to the axis of said cylindrical portion and wherein said cylindrical portion is joined to said collector tube by means of a frusto-conical sidewall.

16. A urine specimen collector assembly according to claim 15 wherein said generally cylindrical portion is tapered from an external diameter larger than the interior of said collector tube at a point adjacent said generally conical sidewall to an exterior diameter less than the diameter of the interior of said collector tube at a point adjacent said collector tube.

* * * * *